United States Patent
Zheng et al.

(10) Patent No.: US 7,482,165 B2
(45) Date of Patent: Jan. 27, 2009

(54) METHOD OF PREVENTING WHITE BLOOD CELL INTERFERENCES TO RED BLOOD CELL MEASUREMENTS OF A BLOOD SAMPLE

(75) Inventors: Min Zheng, Pembroke Pines, FL (US); Jing Li, Miami, FL (US); Yi Li, Miami, FL (US); Michael J. Switzer, Coral Springs, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 629 days.

(21) Appl. No.: 11/210,346

(22) Filed: Aug. 24, 2005

(65) Prior Publication Data

US 2007/0054403 A1    Mar. 8, 2007

(51) Int. Cl.
*G01N 33/48* (2006.01)

(52) U.S. Cl. .............. 436/63; 436/8; 436/10; 436/17; 436/70; 436/174; 436/175; 435/2; 422/73

(58) Field of Classification Search ............ 436/8, 436/10, 63, 70, 17, 174, 175; 435/2; 422/68.1, 422/73
See application file for complete search history.

(56) References Cited

U.S. PATENT DOCUMENTS

| | | |
|---|---|---|
| 2,656,508 A | 10/1953 | Coulter |
| 3,810,011 A | 5/1974 | Coulter et al. |
| 4,521,518 A | 6/1985 | Carter et al. |
| 4,528,274 A | 7/1985 | Carter et al. |
| 5,125,737 A | 6/1992 | Rodriguez et al. |
| 5,554,512 A * | 9/1996 | Lyman et al. .............. 435/69.5 |
| 5,656,499 A | 8/1997 | Chupp et al. |
| 5,763,280 A | 6/1998 | Li et al. |
| 5,834,315 A | 11/1998 | Riesgo et al. |
| 5,882,934 A | 3/1999 | Li et al. |
| 5,891,734 A | 4/1999 | Gill et al. |
| 5,935,857 A | 8/1999 | Riesgo et al. |
| 6,225,124 B1 | 5/2001 | Houwen et al. |
| 6,410,330 B1 | 6/2002 | Li et al. |
| 6,573,102 B2 | 6/2003 | Li et al. |
| 6,706,526 B2 | 3/2004 | Lang et al. |
| 2003/0235917 A1 | 12/2003 | Li et al. |

* cited by examiner

*Primary Examiner*—Maureen M Wallenhorst
(74) *Attorney, Agent, or Firm*—Cuspa Technology Law Associates; Mitchell E. Alter

(57) ABSTRACT

Methods of prevention and correction of white blood cell interferences to the measurements of mean cell volume (MCV), red blood cell concentration (RBC) and hematocrit (Hct) of a blood sample are disclosed. The interference to MCV can be prevented by identifying a valley between the red blood cell and white blood cell modes on the red blood cell distribution histogram, defining a red blood cell region using the valley and calculating MCV within the defined region. Alternatively, a curve fit of the white blood cell population on the red blood cell distribution histogram can be used to exclude the white blood cells. RBC can be corrected by subtracting the white blood cell concentration obtained from the analysis of a second aliquot sample, when the white blood cell concentration (WBC) exceeds a predetermined criterion. Hct of the blood sample can be calculated using the obtained MCV and RBC.

21 Claims, 5 Drawing Sheets

METHOD OF PREVENTING WHITE BLOOD CELL INTERFERENCES TO RED BLOOD CELL MEASUREMENTS OF A BLOOD SAMPLE

FIELD OF THE INVENTION

The present invention relates to a method for preventing and correcting white blood cell interference to red blood cell measurements in a blood sample. More specifically, the methods prevent and correct white blood cell interferences to mean cell volume, red blood cell concentration and hematocrit measurements of a blood sample.

BACKGROUND OF THE INVENTION

Mean cell volume (MCV) of the red blood cells, red blood cell concentration, also commonly referred to red blood cell count (RBC), red cell distribution width (RDW) of a blood sample are directly measured red blood cell parameters by cell counting and sizing on various hematology analyzers. These parameters are measured with a whole blood sample substantially diluted in an isotonic blood diluent, using direct current impedance (DC) or light scatter measurements in a non-focused flow aperture or a focused flow cell. On these hematology analyzers, hematocrit (Hct) is a derivative parameter of RBC and MCV (Hct=RBC×MCV/10).

For the normal population, MCV has a mean value of $90.3 \pm 9.6$ fl and RBC has a mean of $4.3 \times 10^{12}/l$ for adults. The newborn babies have increased MCV, i.e., $101 \pm 13$. Many diseases, such as iron deficiency, Hgb S-alpha or beta thalassemia, Hgb H, folate or vitamin B12 deficiency, sickle cell anemia, immune hemolytic anemia, preleukemia, cause abnormal MCV values, either higher or lower than the normal value. Similarly, many diseases cause abnormally low or high RBC. These, in turn, cause abnormal hematocrit. Therefore, MCV, RBC, and Hct are clinically important parameters, and the accuracy of the measurements of these parameters is essential to clinical diagnosis.

In a normal peripheral blood sample the red blood cell concentration is about 900 times higher than the white blood cell concentration. The contribution of white blood cells to the red blood cell measurements, such as MCV, RBC and Hct, is negligible, although the white blood cells are present in the sample mixture used for the red blood cell measurements. However, when the white blood cell concentration is very high, for example, 200,000/µl to 500,000/µl, the contribution of the white blood cells to the measurements of red blood cell parameters is no longer negligible.

Among the white blood cell subpopulations, the lymphocyte population can interfere with the MCV measurement, because the size of lymphocytes is the closest to the size of red blood cells. The red blood cells have an average cell volume of 90 fl, and the lymphocytes have an average cell volume of 220 fl. Typically, the red blood cells are measured in a range between 0 to 360 fl, and the MCV is calculated in a range from about 30 fl to 360 fl. The other white blood cell subpopulations, such as monocytes and granulocytes are much larger, and they are outside the dynamic range of the red blood cell size measurement, therefore, do not interfere with the MCV calculation.

However, all white blood cell subpopulations can contribute to red blood cell concentration measurement when the white blood cell concentration is substantially higher than the normal value. The interferences from the white blood cells can generate erroneous MCV, RBC and Hct values, and cause confusion or difficulty for diagnosis.

Currently, the clinical practice in handling a high WBC sample is to manually dilute the whole blood sample to reduce the white blood cell concentration down to less than 130,000/µl. Such a dilution can reduce white blood cell interference to hemoglobin measurement by reducing the turbidity caused by the cellular particles. However, the dilution does not change the ratio between the red blood cells to the white blood cells. Upon dilution, the red blood cell concentration in the diluted sample mixture is also reduced. To maintain the measurement accuracy, the hematology analyzers typically extend the count time to ensure sufficient number of events to be counted in the measurement. Since the ratio between the red blood cells to the white blood cells remains the same, the interferences of white blood cells to MCV, RBC and Hct measurements in the diluted sample mixture remain the same.

U.S. Pat. No. 5,656,499 (to Chupp et al) teaches a method of calculating MCV by setting a left and a right discriminants for red blood cell population on the red blood cell histogram. More specifically, the method first determines the mode of the red blood cell histogram, then on either side of the mode, the first bin (or channel) with a population less than 4% of the population of the mode is identified. These channels on the two side of the mode are defined as the discriminants, and only populations between them are used for calculating MCV. Therefore, Chupp et al define the MCV in their method with the equation of MCV=(mean of histogram between discriminants)×(0.8 fl per bin)×(calibration factor). For the RBC count measurement, Chupp et al teach to identify a zero count bin on the left of the red blood cell mode and set it as the count threshold, and the values greater than this threshold are considered to be red blood cells. Chupp et al's method for MCV calculation has disadvantages. When the lymphocytes and red blood cells have a substantial overlap, such as in the situations of small lymphocytes, or leukocytosis with macrocytic anemia, this method could include the lymphocytes between the discriminants, therefore, report erroneous MCV.

It is apparent that there is a need for prevention and correction of white blood cell interferences to the above discussed red blood cell measurements on automated hematology analyzers.

SUMMARY OF THE INVENTION

In one aspect, the present invention is directed to a method of measuring mean cell volume of red blood cells in a blood sample, which prevents the interference of the white blood cells. In one embodiment, the method comprises the steps of: mixing a first aliquot of the blood sample with an isotonic blood diluent to form a first sample mixture; measuring volumes of blood cells in the first sample mixture, and obtaining a red blood cell distribution histogram; determining a red blood cell distribution mode on the red blood cell distribution histogram; determining a white blood cell distribution mode beyond a predetermined limit on the red blood cell distribution histogram; determining a valley between the white blood cell distribution mode and the red blood cell distribution mode; defining a red blood cell region as a region below the valley on the red blood cell distribution histogram; calculating the mean cell volume of the red blood cells in the red blood cell region; and reporting the mean cell volume of the red blood cells in the blood sample.

In a further embodiment, the method further comprises following steps prior to initiating the correction process for preventing white blood cell interference: mixing a second aliquot of the blood sample with a lysing reagent system to lyse red blood cells, and to form a second sample mixture; measuring numbers of white blood cells in the second sample mixture, and obtaining a white blood cell concentration of the blood sample; and if the white blood cell concentration obtained exceeding a predetermined criterion, then initiating the steps starting from determining the white blood cell distribution mode on the red blood cell distribution histogram.

In another embodiment, the method uses curve fitting to prevent the white blood cell interference to the measurement of mean cell volume of red blood cells in a blood sample. The method comprises the steps of: mixing an aliquot of the blood sample with an isotonic blood diluent to form a sample mixture; measuring volumes of blood cells in the sample mixture, and obtaining a red blood cell distribution histogram; identifying a white blood cell population beyond a predetermined limit on the red blood cell distribution histogram; performing a curve fit of the white blood cell population on the red blood cell distribution histogram; subtracting white blood cells under a fitted curve from the red blood cell distribution histogram; calculating the mean cell volume using remaining red blood cells of the red blood cell distribution histogram; and reporting the mean cell volume of the red blood cells in the blood sample.

In a further aspect, the present invention is directed to a method of correcting white blood cell interference to the measurement of red blood cell concentration in a blood sample. In one embodiment, the method comprises the steps of: mixing a first aliquot of the blood sample with an isotonic blood diluent, and to form a first sample mixture; mixing a second aliquot of the blood sample with a lysing reagent system to lyse red blood cells, and to form a second sample mixture; measuring numbers of blood cells in the first sample mixture, and obtaining a total blood cell concentration of the blood sample; measuring numbers of white blood cells in the second sample mixture, and obtaining a white blood cell concentration in the blood sample; subtracting the obtained white blood cell concentration from the total blood cell concentration to obtain the red blood cell concentration of the blood sample; and reporting the red blood cell concentration of the blood sample.

In another aspect, the present invention is directed to a method of measuring hematocrit in a blood sample. The method uses the mean cell volume of red blood cells and red blood cell concentration obtained using the methods of the present invention to calculate hematocrit, therefore, prevents the white blood cell interference to hematocrit.

BRIEF DESCRIPTION OF DRAWINGS

FIG. 4B shows a Gaussian fit of the white blood cell population.

FIG. 5B shows a Gaussian fit of the white blood cell population.

DETAILED DESCRIPTION OF THE INVENTION

Figure 1A:
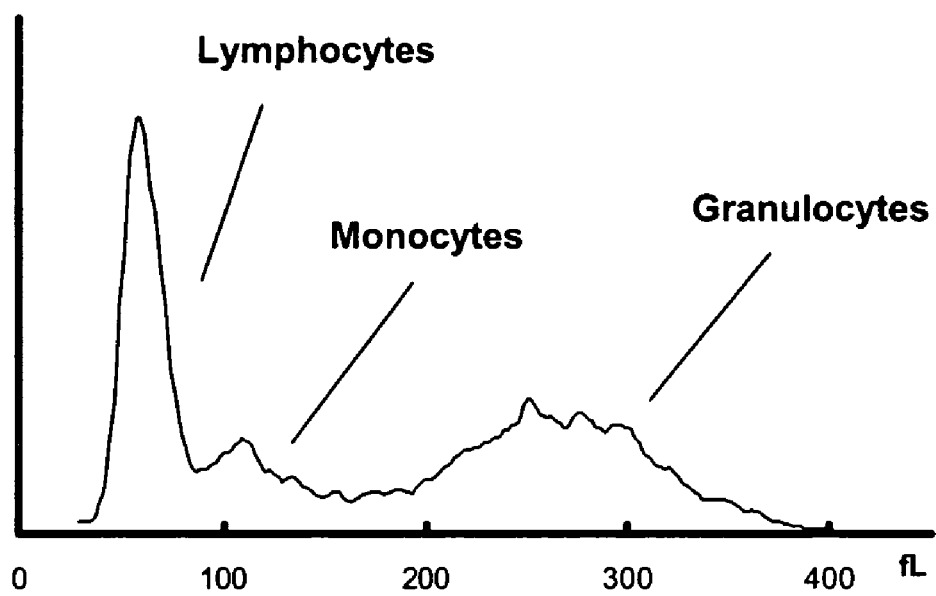
FIG. 1A and FIG. 1B are the white blood cell and red blood cell distribution histograms of a normal blood sample obtained using the process described in Example 1.

In one embodiment, the present invention provides a method using a correction process to prevent white blood cell interference to the measurement of mean cell volume (MCV) of red blood cells in a blood sample.

The term of correction process used herein refers to one or more sample analysis processes which either prevent or correct the contribution of the white blood cells to the measurements of specific red blood cell parameters.

The method includes following steps: (a) mixing an aliquot of the blood sample with an isotonic blood diluent to form a sample mixture; (b) measuring volumes of blood cells in the sample mixture, and obtaining a red blood cell distribution histogram; (c) determining a red blood cell distribution mode on the red blood cell distribution histogram; (d) determining a white blood cell distribution mode beyond a predetermined limit on the red blood cell distribution histogram; (e) determining a valley between the white blood cell distribution mode and the red blood cell distribution mode; (f) defining a red blood cell region as a region below the valley on the red blood cell distribution histogram; (g) calculating the mean cell volume of the red blood cells in the red blood cell region; and (h) reporting the mean cell volume of the red blood cells in the blood sample.

For measuring the red blood cells a blood sample is typically diluted substantially with a diluent in a sample chamber or bath. Using an impedance measurement with a non-focused flow aperture, the blood sample can be diluted with a dilution ratio of 6250:1. When a focused flow cell is used for the measurement, the dilution ratio can be substantially lower, such as 290:1. To maintain red blood cell volume and morphology during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526.

When a particle or a blood cell, suspended in a conductive solution, passes through a flow cell or an aperture, an electrical signal, or a pulse, can be measured due to the increase of impedance. The electrical pulses have been used for counting the numbers of red blood cells, platelets and white blood cells in the sample mixtures of a blood sample.

On the other hand, the pulse shape, height and width are directly related to the volume or size of a particle, and can be converted to the volume of the cell measured. When a sample that contains two or more different blood cells having different volumes is measured, a histogram obtained from the measurement can represent volume distribution of these blood cells. The detection methods and apparatus used for blood cell counting and sizing by a blood analyzer equipped with a DC impedance measurement device are generally described in U.S. Pat. Nos. 2,656,508, 3,810,011 and 5,125,737, which are hereby incorporated by reference in their entirety. Herein, the phrase "blood cell sizing" refers to the cell volume measurement.

Alternatively, low angle light scatter measurement can also be used for counting and sizing the blood cells. Herein, the term "low angle light scatter" refers to light scatter signals measured in a range in less than 10° from the incident light.

In the cell volume measurement, a cell volume distribution histogram is obtained. For the red blood cell measurement, the obtained histogram is referred to as the red blood cell distribution histogram. For a normal blood sample, a narrow and well defined red blood cell distribution, typically a Gaussian distribution, is obtained. For clinically abnormal blood samples, various distortions of the distribution have been observed, such as shift of the distribution to either higher or lower volume side, asymmetric distribution, population extension on either the higher or lower volume side, or both sides. For certain clinical conditions or blood transfusion patients, two distinct red blood cell distribution peaks can be present. However, even with the most severely distorted red blood cell distribution, the red blood cells distribute in a range that is less than 200 femtoliters (fl).

When the white blood cell concentration in a blood sample is very high, for example from 200,000/µl to 500,000/µl, particularly when lymphocyte percentage is also high, such as in the blood sample of leukocytosis patients, the lymphocytes appear as an additional cell distribution on the right side of the red blood cells, starting from about 160 fl or higher, typically having its mode in a range from about 210 fl to about 270 fl. In the presence of the additional white blood cell distribution in the red blood cell histogram, the mean cell volume calculation of the red blood cells can be interfered by the additional cell distribution, which can result in a substantial increase of the obtained MCV value. It has been found that when white blood cell concentration is equal or above 130,000/µl, the white blood cell contribution can start to affect the accuracy of the MCV measurement.

The correction process used in the method of the present invention uses an algorithm to first determine the red blood cell distribution mode, and then search for and identify the white blood cell distribution mode beyond a predetermined limit in the red blood cell distribution histogram. If the white blood cell distribution mode is determined, the algorithm further searches for and identifies a valley between the red blood cell distribution mode and the white blood cell distribution mode. The term "valley" used herein refers to a channel, of the list mode data, which has a minimum value between the two modes. This valley is used to define the high end of a red blood cell region for calculating MCV. The red blood cell region is defined as a region below the valley. Upon defining the red blood cell region, a MCV is calculated using only the red blood cells within the defined region. Therefore, the white blood cells are excluded from the calculation of MCV, and their interference to the MCV calculation is prevented.

It should be understood that at the low end of the red blood cell histogram, the red blood cell region may, or may not start from the threshold of the volume measurement. Typically, the platelets in the blood sample are measured together with the red blood cells, therefore, the red blood cell region starts above the platelet region. Various techniques and methods are known in the art for differentiating platelets and red blood cells when they are measured together in one sample mixture. These techniques can be used with the instant method.

The term "predetermined limit" used herein refers to a channel on the red blood cell distribution histogram, which is within a range starting from or above the red blood cell distribution mode to below the valley between the white blood cell distribution mode and the red blood cell distribution mode. This channel can be determined based on a large blood sample data base which includes normal blood and various clinical abnormal blood samples. In one preferred embodiment, the predetermined limit is set at about 160 fl, which is above the red blood cell distribution mode. Alternatively, the predetermined limit can be simply set at the red blood cell distribution mode. The valley for most clinical samples which contain extremely high white blood cells, has been found in a range from about 170 fl to about 210 fl. It is noted that each channel on the red blood cell distribution histogram corresponds to a specific volume of the blood cells, hence, it is defined herein by the volume of the blood cells. It should be understood that the numbers of channels in a histogram vary with the dynamic range and resolution of the measurement, therefore, the volume of a blood cell can be expressed by different channel numbers depending on the specific measurement conditions used, however, the absolute volume of the blood cell does not change with these conditions.

Figure 2A:
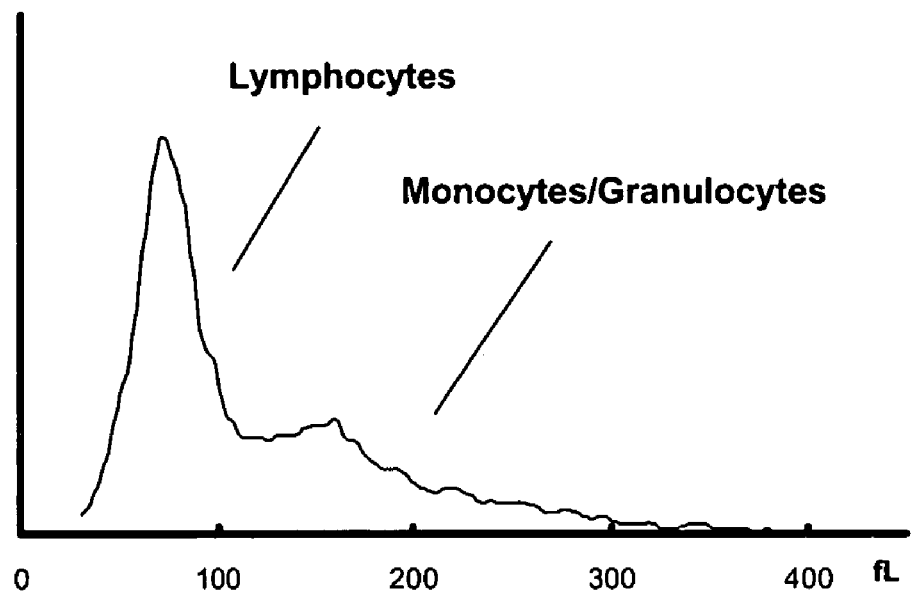
FIG. 2A and FIG. 2B are the white blood cell and the red blood cell distribution histograms of a clinical blood sample which has an extremely high white blood cell concentration, and an abnormally high lymphocyte percentage.
Figure 2B:
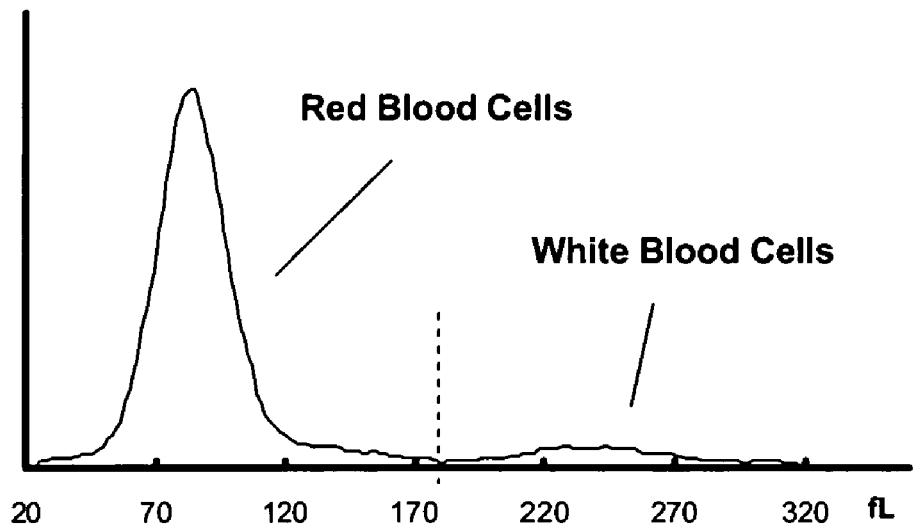
Figure 3A:
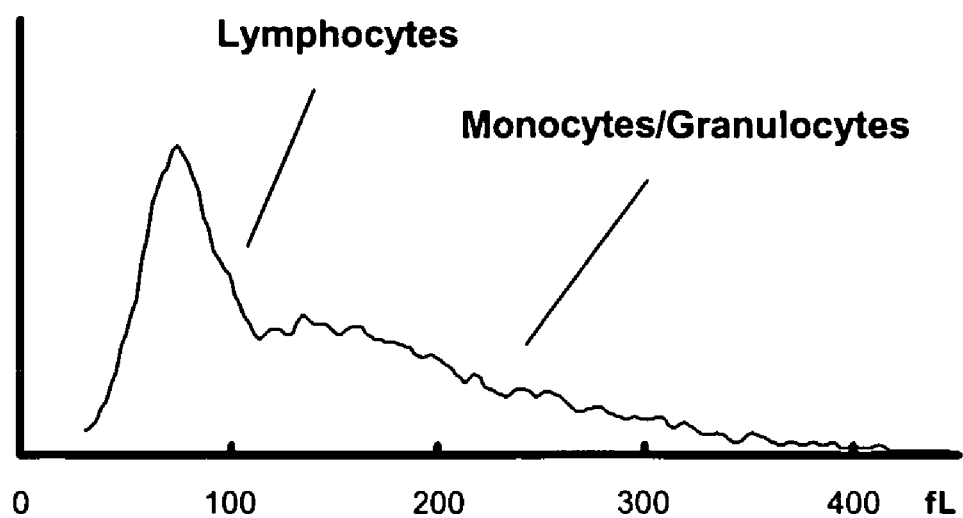
FIG. 3A and FIG. 3B are the white blood cell and the red blood cell distribution histograms of another clinical blood sample which has an extremely high white blood cell concentration, and an abnormally high lymphocyte percentage.
Figure 3B:
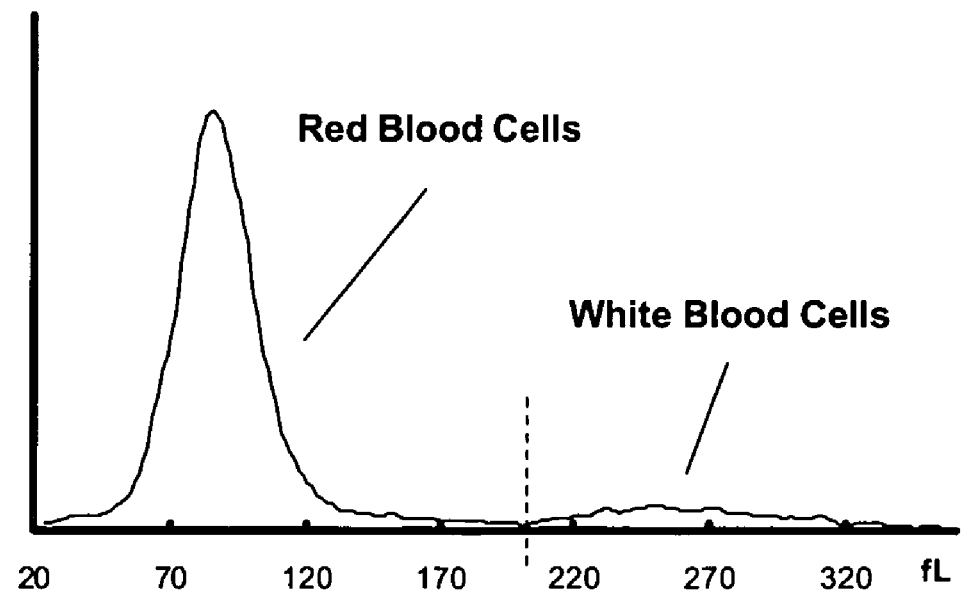

Example 1 illustrates an example using the method of the present invention to prevent the interference of white blood cells to the MCV measurement of two clinical blood samples. Both blood samples had a substantially high white blood cell concentration, i.e., 247,500/µl and 303,600/µl, respectively. As shown in FIGS. 2A and 3A, these blood samples also had extreme high percentage of lymphocytes. FIGS. 2B and 3B show that in each of these two clinical samples a significant white blood cell population was present on the red blood cell histogram. Using the method described above, substantial interferences from the white blood cells, 19.2% and 16.9%, respectively, in the measurement of these two blood samples, can be effectively prevented.

In a further embodiment, the method of the present invention utilizes curve fitting to prevent the interference of the white blood cells to the calculation of the MCV. More specifically, the method includes following steps: (a) mixing an aliquot of the blood sample with an isotonic blood diluent to form a sample mixture; (b) measuring volumes of blood cells in the sample mixture, and obtaining a red blood cell distribution histogram; (c) determining a red blood cell distribution mode on the red blood cell distribution histogram; (d) determining the presence of the white blood cell population beyond a predetermined limit on the red blood cell distribution histogram; (e) performing a curve fit of the white blood cell population on the red blood cell distribution histogram; (f) subtracting white blood cells under the fitted curve obtained in step (e) from the red blood cell distribution histogram; (g) calculating the mean cell volume from the remaining blood cells of the red blood cell distribution histogram after step (f); and (h) reporting the mean cell volume of the red blood cells in the blood sample.

Figure 4A:
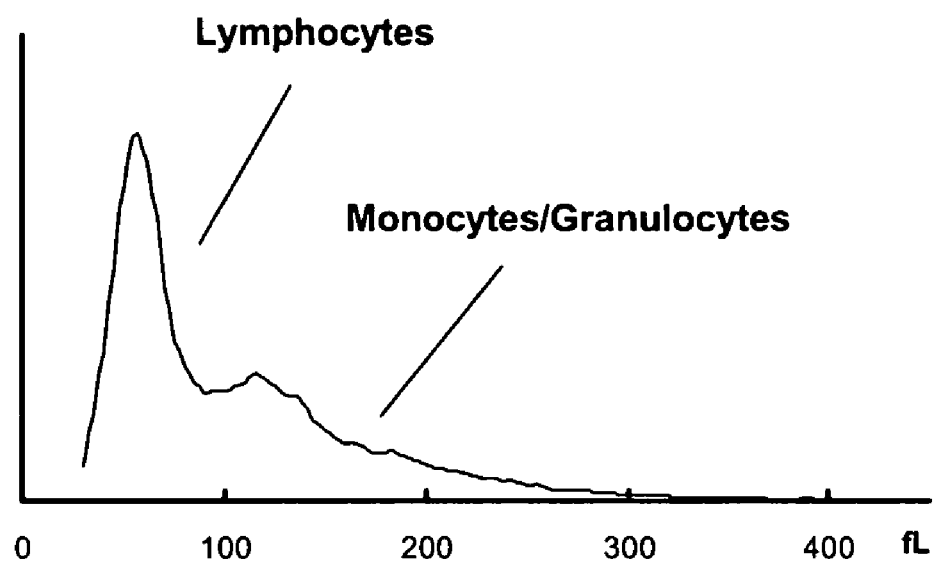
FIG. 4A and FIG. 4B are the white blood cell and the red blood cell distribution histograms of a clinical blood sample which has an extremely high white blood cell concentration.
Figure 4B:
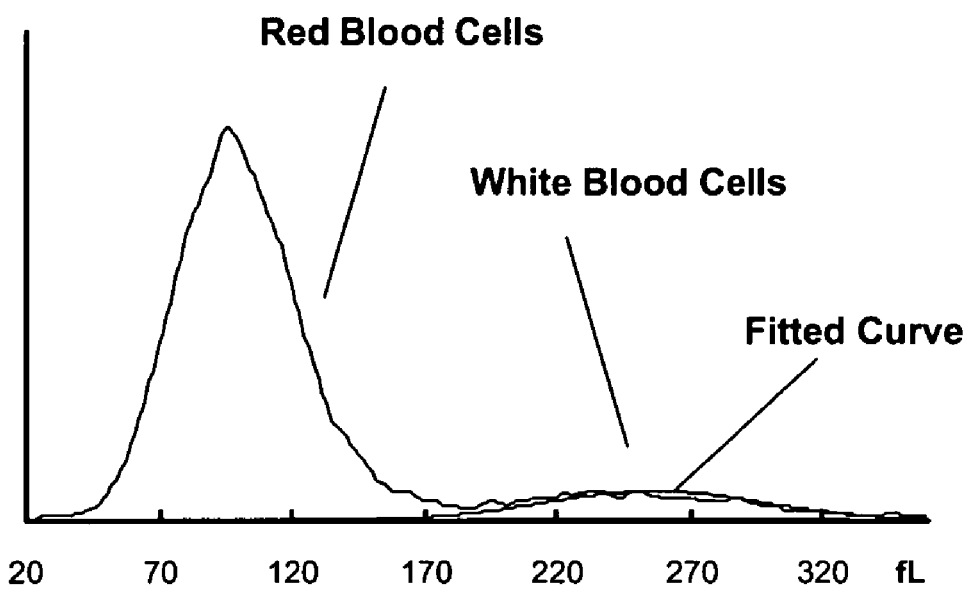
Figure 5A:
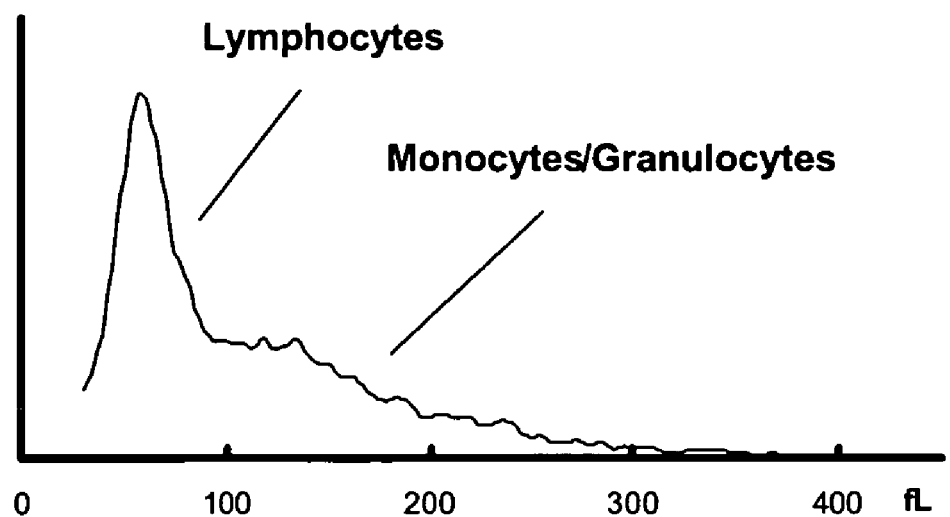
FIG. 5A and FIG. 5B are the white blood cell and the red blood cell distribution histograms of another clinical blood sample which has an extremely high white blood cell concentration.
Figure 5B:
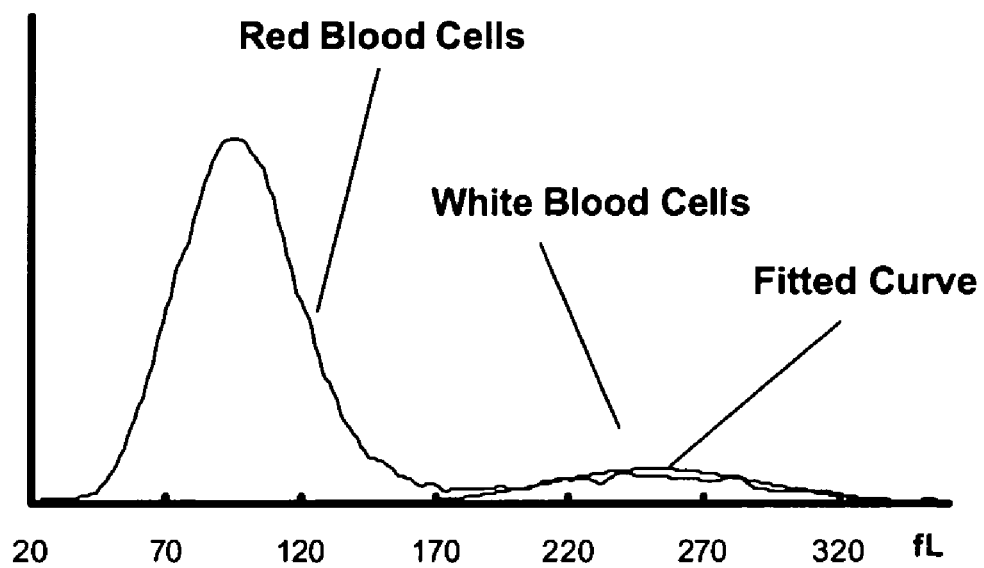

It is apparent that the steps (a) to (c) of these two approaches are the same. In the curve fitting method, in the step (d), the presence of the white blood cell population in the red blood cell distribution histogram can be determined by identifying the mode of the white blood cell population on the histogram beyond the predetermined limit. The curve fitting of the white blood cell population can be a Gaussian fit or other suitable curve fitting methods. Example 2 illustrates the use of a Gaussian fit to prevent the interference of the white blood cells to the MCV calculation of the red blood cells. As shown in FIGS. 4B and 5B, after performing a Gaussian fit, the white blood cell population under the fitted curve is subtracted from the whole histogram. Only the remaining red blood cells are used for calculation of MCV.

The curve fitting method can be used independently, or together with, the method described above, and it is particularly useful in the situation that the white blood cells substantially overlap with the red blood cells, and the determination of the valley between the two modes is difficult. Therefore, in a further embodiment, a combination of the two methods described above is provided, as illustrated by the following flow diagram.

In the combined approach, a predetermined criterion for an acceptable valley can be further provided. If the criterion is met, the method defines the red blood cell region and calculates MCV using the population within the region as described above, otherwise, the method performs a curve fit to exclude the white blood cells as described above, and then calculates MCV using the remaining red blood cells. In one embodiment, the predetermined criterion is defined by the ratio of the amplitude of the valley to the amplitude of the red blood cell distribution mode. For example, if the amplitude of the valley is higher than 2% of the amplitude of the red blood cell distribution mode, the curve fitting method will be used. Other suitable criteria can also be used.

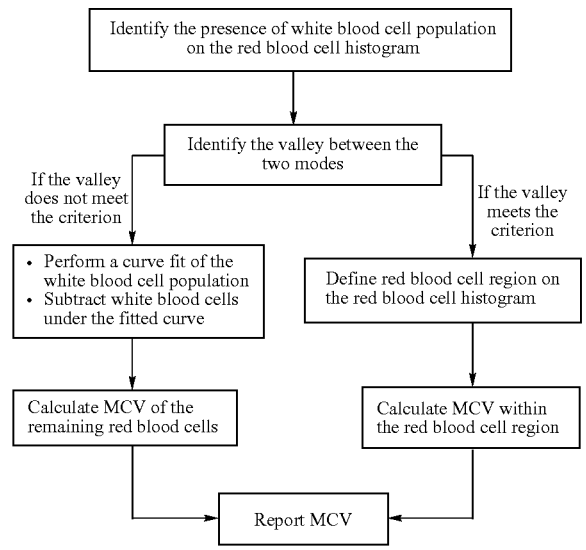

In yet a further embodiment, the method of the present invention can further utilize the information from a concurrent white blood cell measurement commonly performed on the automated hematology analyzer. In this method, only when the white blood cell measurement indicates a substantially elevated white blood cell concentration in the blood sample, the correction process described above for preventing the white blood cell interference to MCV calculation is initiated, instead of performing the correction process to every sample. The method steps can be described as follows: (a) mixing first aliquot of the blood sample with an isotonic blood diluent to form a first sample mixture; (b) mixing a second aliquot of the blood sample with a lysing reagent system to lyse red blood cells, and to form a second sample mixture; (c) measuring volumes of blood cells in the first sample mixture, obtaining a red blood cell distribution histogram and determining a red blood cell distribution mode; (d) measuring numbers of white blood cells in the second sample mixture, and obtaining a white blood cell concentration of the blood sample; (e) if the white blood cell concentration obtained in step (d) exceeding a predetermined criterion, identifying a white blood cell distribution mode beyond a predetermined limit on the red blood cell distribution histogram; (f) identifying a valley between the white blood cell distribution mode and the red blood cell distribution mode; (g) defining a red blood cell region on the red blood cell distribution histogram as a region bellow the valley; (h) calculating the mean cell volume of the red blood cells within the red blood cell region; and (i) reporting the mean cell volume of the red blood cells in the blood sample. Alternatively, the curve fitting method can be used, either independently or in combination with the method defining the valley and the red blood cell region, as described above.

Preferably, the predetermined criterion described in step (e) is set as white blood cell concentration being equal or above 130,000/µl. When the white blood cell concentration obtained from the measurement of the second sample mixture exceeds the predetermined criterion, the correction process is initiated in the analysis of the red blood cell distribution histogram for calculation of MCV.

Typically, the white blood cell concentration, which is also commonly referred as white blood cell count (WBC), of the blood sample is measured with a total dilution ratio of 250:1. Furthermore, a differential analysis of the white blood cell subpopulations can be also performed at the same time. The absolute concentrations of white blood cell subpopulations can be obtained by combining the result of differential analysis and the total white blood cell concentration. The white blood cell concentration measurement and the differential analysis can be obtained using impedance or light scatter measurements.

One lysing reagent system suitable for lysing red blood cells in the second sample mixtures comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102, these are hereby incorporated by reference in their entirety. Alternatively, the reagent system can also be an isotonic lysing reagent as described in U.S. Pat. No. 5,882,934 which is hereby incorporated by reference in its entirety. This reagent lyses the red blood cells and dilutes the blood sample at the same time for subsequent white blood cell analysis.

In a further aspect, the present invention provides a method of correction of white blood cell interference to the measurement of red blood cell concentration (RBC) in a blood sample. More specifically, the method includes the steps of: (a) mixing a first aliquot of a blood sample with an isotonic blood diluent to form a first sample mixture; (b) mixing a second aliquot of the blood sample with a lysing reagent system to lyse red blood cells, and to form a second sample mixture; (c) measuring numbers of blood cells in the first sample mixture, and obtaining a total blood cell concentration of the blood sample; (d) measuring numbers of white blood cells in the second sample mixture, and obtaining a white blood cell concentration in the blood sample; (e) subtracting the white blood cell concentration obtained in step (d) from the total blood cell concentration to obtain the red blood cell concentration of the blood sample; and (f) reporting the red blood cell concentration of the blood sample. Furthermore, the step (e) can be conditionally initiated, for example, only when the white blood cell concentration exceeds a predetermined criterion, the subtraction is performed.

The total blood cell concentration in the first sample mixture can be obtained using the diluent and the method described above in the red blood cell measurement. The total blood cell concentration is also referred to herein as raw RBC. It should be understood that for a normal blood sample the total blood cell concentration obtained in the first sample mixture is the red blood cell concentration of the blood sample, because the white blood cell concentration is negligible. For a clinical sample having a very high WBC, the total blood cell concentration in the first sample mixture includes the contributions from both red blood cells and white blood cells. Furthermore, it should be understood that the numbers of blood cells in the first sample mixture measured and the obtained total blood cell concentration in step (c) do not include platelets. The platelets can be measured in a concurrent measurement of the first sample mixture, however, they are distinguished from the red blood cells.

As described above, the dilution ratios for the red blood cell and for the white blood cell measurements can be substantially different. In step (e), both white blood cell concentration and total blood cell concentration are the respective concentrations in the blood sample, not the concentrations in the second and the first sample mixtures, respectively.

For correction of red blood cell concentration, the predetermined criterion for initiating the correction is typically lower than the criterion used for MCV calculation, since a white blood cell concentration of 50,000/µl can start to affect the accuracy of RBC measurement.

As described in detail in Example 1, in an exemplary embodiment, the second aliquot blood sample is diluted by an isotonic diluent, and mixed with a lysing reagent to form a second sample mixture. The second sample mixture is drawn into a set of three non-focused flow apertures by a vacuum source, and the white blood cell concentration is measured by impedance measurement. The white blood cells are also differentiated into three subpopulations using an impedance measurement, i.e., lymphocytes, monocytes and granulocytes.

Example 1 shows the results of correcting the white blood cell interference to the red blood cell concentration measurement. As shown, the white blood cell concentrations of the two clinical samples were 247,500/µl and 303,600/µl, respectively. The total blood cell concentrations measured in the first sample mixture were $1.97 \times 10^{12}/l$ and $2.53 \times 10^{12}/l$, respectively. After correction of the white blood cell contribution, the obtained RBCs were $1.72 \times 10^{12}/l$ and $2.23 \times 10^{12}/l$, respectively. The correction effectively eliminated contributions of 14.5% and 13.5%, respectively, of the white blood cells present in the first sample mixture.

In another aspect, the present invention provides a method of preventing white blood cell interference to the measurement of hematocrit (Hct) of a blood sample. The method uses MCV and RBC obtained using the methods of the present invention, as described above, to calculate Hct, therefore, eliminates the white blood cell interference to Hct.

More specifically, the method steps can be described as follows: (a) mixing a first aliquot of a blood sample with an isotonic blood diluent to form a first sample mixture; (b) mixing a second aliquot of the blood sample with a lysing reagent system to lyse red blood cells, and to form a second sample mixture; (c) measuring numbers and sizes of blood cells in the first sample mixture, obtaining a total blood cell concentration of the blood sample and a red blood cell distribution histogram, and determining a red blood cell distribution mode; (d) measuring numbers of white blood cells in the second sample mixture, and obtaining a white blood cell concentration in the blood sample; (e) identifying a white blood cell distribution mode beyond a predetermined limit on the red blood cell distribution histogram obtained from the first sample mixture; identifying a valley between the white blood cell distribution mode and a red blood cell distribution mode; defining a red blood cell region on the blood cell distribution histogram as a region bellow the valley; calculating the mean cell volume of the red blood cells within the red blood cell region; (f) subtracting the white blood cell concentration obtained in step (d) from the total blood cell concentration obtained in step (c) to obtain the red blood cell concentration of the blood sample; (g) obtaining hematocrit of the blood sample by multiplying the red blood cell concentration obtained in step (f) by the mean cell volume obtained in step (e); and (h) reporting the hematocrit of the blood sample. Alternatively, the curve fitting method can be used for calculation of MCV, either independently or in combination with the method defining the valley and the red blood cell region, as described above. Furthermore, as described previously, the step (f) can be conditionally initiated, such as only when the white blood cell concentration exceeds a predetermined criterion.

As can be appreciated, since hematocrit is a derivative parameter of MCV and RBC, the white blood cell interference to the measurement of hematocrit in a blood sample can be prevented by using the methods of the present invention for measurements of MCV and RBC. To implement the correction processes to the measurements of the three red blood cell parameters described above in an automated blood analysis of a blood sample, several options of selecting the predetermined criterion of the white blood cell count are available. One option is not to set a criterion on the white blood cell count, hence, the correction processes described above are applied to each sample. Another option is to select the predetermined criterion for the correction of RBC for both RBC and the MCV correction processes, since the criterion for RBC correction is lower. A further option is to select two different criteria for the RBC and MCV correction processes, for example, using 50,000 µl of WBC for initiating the RBC correction, and 130,000/µl of WBC for initiating MCV correction, respectively.

As a further aspect of the present invention, using MCV, RBC and Hct obtained by the method of the present invention, white blood cell interference to other derivative parameters, such as mean corpuscular hemoglobin (MCH) and mean corpuscular hemoglobin concentration (MCHC), can also be prevented. Herein, MCH=Hgb/RBC; and MCHC=Hgb/Hct (Hgb refers to the hemoglobin concentration of the blood sample). It is noted that the hemoglobin concentration can be obtained using the methods known in the art.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

A hematology analyzer which had a RBC chamber and a WBC chamber, each equipped with three non-focused flow apertures, was used for analysis of the blood samples. The hematology analyzer measures numbers and volumes of red blood cells and white blood cells in a blood sample by direct current (DC) impedance measurements. The analyzer also provides a 3-part differential analysis of white blood cells in a blood sample, which differentiates white blood cells into three subpopulations, i.e., lymphocytes, monocytes and granulocytes. An isotonic diluent, Isoton® 3E (product of Beckman Coulter, Inc., Florida) was used to dilute the first and the second aliquots of the blood sample. A lysing reagent, Lyse S III diff (product of Beckman Coulter, Inc., Florida) was used to lyse red blood cells in the second sample mixture.

A first aliquot of 1.6 µl of a blood sample was diluted by Isoton 3E in the RBC chamber with a dilution ratio of 6250:1, to form a first sample mixture. The first sample mixture was measured by DC impedance measurements to produce a red blood cell distribution histogram and the red blood cell count. A second aliquot of 28 µl of the blood sample was diluted with 6 ml of Isoton 3E, and then mixed with 1 ml of Lyse S III diff to form a second sample mixture. The second sample mixture was measured by DC impedance measurements to produce a white blood cell distribution histogram and the white blood cell count.

Figure 1B:
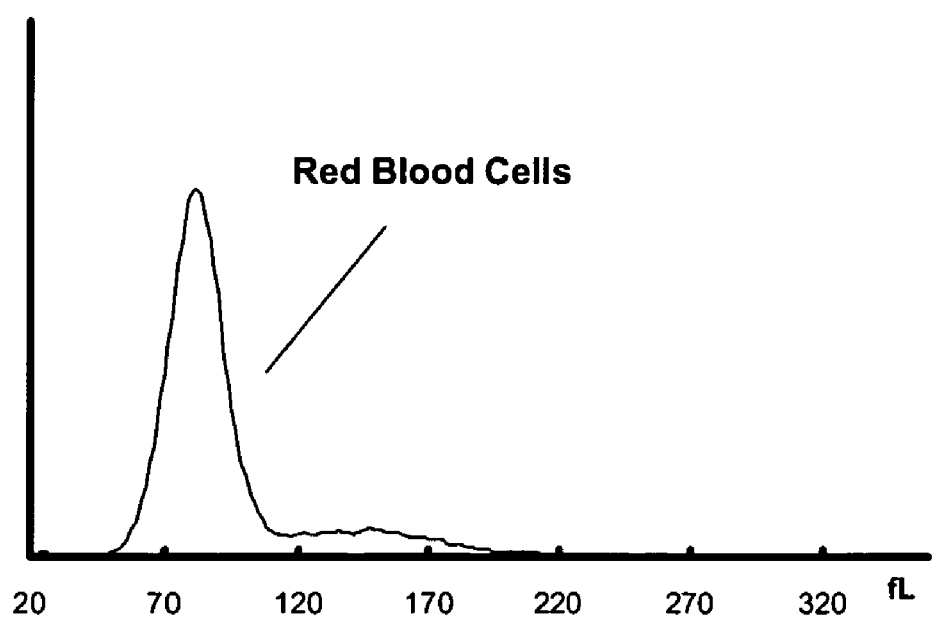

FIGS. 1A and 1B show the white blood cell and red blood cell histograms of a normal blood sample obtained on the hematology analyzer. It is noted that in the normal blood sample the tail on the right side of the red blood cell distribution mode is a distortion typically observed when a non-focused flow aperture is used, which is due to the trajectory variation when cells pass through the aperture. With certain clinical samples, the amplitude of the tail increases because of the presence of macrocytic cells, sickle cells, and etc. However, the position of the tail on the red blood cell distribution histogram is below the white blood cell population.

Two clinical whole blood samples were analyzed on the hematology analyzer as described above. The white blood cell measurement reported that these two samples had WBC of 247,500/µl and 344,800/µl, respectively. FIGS. 2A and 3A show the white blood cell histograms of these two samples, and in each case, the lymphocyte subpopulation had an abnormally high percentage. The white blood cell differential analysis reported 60.6% and 44.9% of lymphocytes in these two samples, respectively. FIGS. 2B and 3B show the red blood cell histograms of these two samples. As shown, there was a distinct white blood cell population on the right side of the red blood cells on each histogram.

The red blood cell histogram was analyzed using the correction process described above to determine the red blood cell and white blood cell modes, identify the valley between the modes (as indicated by the dotted line on FIGS. 2B and 3B), define the red blood cell region (the region on the left of the dotted line), and calculate MCV within the defined red blood cell region. On the other hand, the WBC was subtracted from the total blood cell concentration obtained from the measurement of the first sample mixture (or raw RBC), to produce the corrected, or true RBC of the blood sample. Hct of the blood sample was then calculated using the obtained MCV and RBC.

Table 1 shows the obtained results, which illustrates effective prevention and correction of the white blood cell interferences to MCV, RBC and Hct.

TABLE 1

|  | If no correction | After correction | Potential white blood cell contribution |
|---|---|---|---|
| Sample 1, WBC = 247,500/µl | | | |
| MCV (fl) | 97.6 | 81.9 | 19.2% |
| RBC ($10^{12}$/l) | 1.97 | 1.72 | 14.5% |
| Hct | 19.2 | 14.1 | 36.2% |
| Sample 2, WBC = 303,600/µl | | | |
| MCV (fl) | 102.8 | 84.0 | 22.4% |
| RBC ($10^{12}$/l) | 2.34 | 2.00 | 17.0% |
| Hct | 24.1 | 16.8 | 43.5% |

EXAMPLE 2

Another two clinical whole blood samples were analyzed on the hematology analyzer as described in Example 1. The white blood cell measurement reported that these two samples had WBC of 303,600/µl and 309,900/µl, respectively. FIGS. 4A and 5A show the white blood cell histograms of these two samples. The white blood cell differential analysis reported 50.1% and 55.2% of lymphocytes in these two samples, respectively.

FIGS. 4B and 5B show the red blood cell histograms of these two samples. As shown, the valleys for these two samples were not as low as those observed in Example 1, and there was a certain level of overlap between the white blood cell population and the red blood cell population on each histogram.

The red blood cell histograms were analyzed using a Gaussian fit process. FIGS. 4B and 5B show the Gaussian fit for the white blood cell population. The white blood cells under the fitted curve were subtracted from the total numbers of cells under the overall distribution curve, and the remaining red blood cells were used for calculating MCV. Table 2 shows the obtained results, which illustrates effective prevention and correction of the white blood cell interferences to MCV, RBC and Hct.

TABLE 2

|  | If no correction | After correction | Potential white blood cell contribution |
|---|---|---|---|
| Sample 3, WBC = 303,600/µl | | | |
| MCV (fl) | 109.4 | 96.5 | 13.4% |
| RBC ($10^{12}$/l) | 2.53 | 2.23 | 13.5% |
| Hct | 27.7 | 21.5 | 28.8% |
| Sample 4, WBC = 309,900/µl | | | |
| MCV (fl) | 107.9 | 93.9 | 14.9% |
| RBC ($10^{12}$/l) | 2.39 | 2.08 | 14.9% |
| Hct | 25.8 | 19.5 | 32.3% |

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of measuring mean cell volume of red blood cells in a blood sample comprising the steps of:
    (a) mixing a first aliquot of said blood sample with an isotonic blood diluent to form a first sample mixture;
    (b) measuring volumes of blood cells in said first sample mixture, and obtaining a red blood cell distribution histogram;
    (c) determining a red blood cell distribution mode on said red blood cell distribution histogram;
    (d) determining a white blood cell distribution mode beyond a predetermined limit on said red blood cell distribution histogram;
    (e) determining a valley between said white blood cell distribution mode and said red blood cell distribution mode;
    (f) defining a red blood cell region as a region below said valley on said red blood cell distribution histogram;
    (g) calculating said mean cell volume of said red blood cells in said red blood cell region; and
    (h) reporting said mean cell volume of said red blood cells in said blood sample.

2. The method of claim 1 wherein said predetermined limit is a channel from or above said red blood cell distribution mode and to below said valley.

3. The method of claim 2 wherein said predetermined limit is about 160 fl.

4. The method of claim 1 wherein said red blood cell region is above a platelet region.

5. The method of claim 1 further comprising the steps (i)-(k) prior to step (d)
   (i) mixing a second aliquot of said blood sample with a lysing reagent system to lyse red blood cells, and to form a second sample mixture;
   (j) measuring numbers of white blood cells in said second sample mixture, and obtaining a white blood cell concentration of said blood sample; and
   (k) if said white blood cell concentration obtained in step (j) exceeding a predetermined criterion, then initiating step (d).

6. The method of claim 5 wherein said predetermined criterion is 130,000 white blood cells per microliter of a blood sample.

7. The method of claim 1 further comprising:
   (i) measuring numbers of blood cells in said first sample mixture, and obtaining a total blood cell concentration of said blood sample;
   (j) mixing a second aliquot of said blood sample with a lysing reagent system to lyse red blood cells, and to form a second sample mixture;
   (k) measuring numbers of white blood cells in said second sample mixture, and obtaining a white blood cell concentration in said blood sample;
   (l) subtracting said white blood cell concentration obtained in step (k) from said total blood cell concentration obtained in step (i) to obtain said red blood cell concentration of said blood sample; and
   (m) reporting said red blood cell concentration of said blood sample.

8. A method of measuring mean cell volume of red blood cells in a blood sample comprising the steps of:
   (a) mixing an aliquot of said blood sample with an isotonic blood diluent to form a first sample mixture;
   (b) measuring volumes of blood cells in said first sample mixture, and obtaining a red blood cell distribution histogram;
   (c) identifying a white blood cell population beyond a predetermined limit on said red blood cell distribution histogram;
   (d) performing a curve fit of said white blood cell population on said red blood cell distribution histogram;
   (e) subtracting white blood cells under a fitted curve obtained in step (d) from said red blood cell distribution histogram;
   (f) calculating said mean cell volume using remaining red blood cells of said red blood cell distribution histogram after step (e); and
   (g) reporting said mean cell volume of said red blood cells in said blood sample.

9. The method of claim 8 wherein said predetermine limit is a channel from or above a red blood cell distribution mode on said red blood cell distribution histogram.

10. The method of claim 8 further comprising the steps (h)-(j) prior to step (c):
    (h) mixing a second aliquot of said blood sample with a lysing reagent system to lyse red blood cells, and to form a second sample mixture;
    (i) measuring numbers of white blood cells in said second sample mixture, and obtaining a white blood cell concentration of said blood sample; and
    (j) if said white blood cell concentration obtained in step (i) exceeding a predetermined criterion, then initiating step (c).

11. The method of claim 10 wherein said predetermined criterion is 130,000 white blood cells per microliter of a blood sample.

12. The method of claim 8 further comprising:
    (h) measuring numbers of blood cells in said first sample mixture, and obtaining a total blood cell concentration of said blood sample;
    (i) mixing a second aliquot of said blood sample with a lysing reagent system to lyse red blood cells, and to form a second sample mixture;
    (j) measuring numbers of white blood cells in said second sample mixture, and obtaining a white blood cell concentration of said blood sample;
    (k) subtracting said white blood cell concentration obtained in step (j) from said total blood cell concentration obtained in step (h) to obtain said red blood cell concentration of said blood sample; and
    (l) reporting said red blood cell concentration of said blood sample.

13. A method of correcting white blood cell interference to measurement of red blood cell concentration and mean cell volume of red blood cells in a blood sample on an automated hematology analyzer comprising the steps of;
    (a) mixing a first aliquot of said blood sample with an isotonic blood diluent, to form a first sample mixture;
    (b) mixing a second aliquot of said blood sample with a lysing reagent system to lyse red blood cells to form a second sample mixture;
    (c) measuring numbers and volumes of blood cells in said first sample mixture, and obtaining a total blood cell concentration of said blood sample and a red blood cell distribution histogram;
    (d) measuring numbers of white blood cells in said second sample mixture, and obtaining a white blood cell concentration in said blood sample;
    (e) comparing said white blood cell concentration obtained in step (d) to a first predetermined criterion, and when said white blood cell concentration exceeds said first predetermined criterion, subtracting said white blood cell concentration from said total blood cell concentration obtained in step (c) to obtain said red blood cell concentration of said blood sample;
    (f) comparing said white blood cell concentration obtained in step (d) to a second predetermined criterion, and when said white blood cell concentration exceeds said second predetermined criterion, determining a mean cell volume of said red blood cells using said red blood cell distribution histogram with a correction process to correct a contribution of said white blood cells to said mean cell volume; and
    (g) reporting said red blood cell concentration and said mean cell volume of said red blood cells in said blood sample on said hematology analyzer.

14. The method of claim 13 wherein said first predetermined criterion is 50,000 white blood cells per microliter of a blood sample.

15. The method of claim 13 wherein said second predetermined criterion is 130,000 white blood cells per microliter of a blood sample.

16. The method of claim 13 wherein said measuring numbers of blood cells in said first sample mixture is performed using an impedance measurement.

17. The method of claim 13 wherein said mixing said second aliquot of said blood sample with a lysing reagent system comprises diluting said second aliquot of said blood sample with a blood diluent to form a diluted blood sample, and then mixing said diluted blood sample with a lytic reagent.

18. The method of claim 13 wherein said mixing said second aliquot of said blood sample with a lysing reagent system comprises mixing said second aliquot of said blood sample with a lytic reagent to simultaneously dilute said second aliquot of said blood sample and lyse said red blood cells.

19. A method of measuring hematocrit in a blood sample comprising the steps of:
   (a) mixing a first aliquot of said blood sample with an isotonic blood diluent to form a first sample mixture;
   (b) mixing a second aliquot of said blood sample with a lysing reagent system to lyse red blood cells, and to form a second sample mixture;
   (c) measuring numbers and sizes of blood cells in said first sample mixture, and obtaining a red blood cell distribution histogram and a total blood cell concentration of said blood sample
   (d) measuring numbers of white blood cells in said second sample mixture, and obtaining a white blood cell concentration in said blood sample;
   (e) determining a red blood cell distribution mode on said red blood cell distribution histogram; determining a white blood cell distribution mode beyond a predetermined limit on said red blood cell distribution histogram; determining a valley between said white blood cell distribution mode and said red blood cell distribution mode; defining a red blood cell region on said blood cell distribution histogram as a region below said valley; calculating mean cell volume of said red blood cell within said red blood cell region;
   (f) subtracting said white blood cell concentration obtained in step (d) from said total blood cell concentration obtained in step (c) to obtain said red blood cell concentration of said blood sample;
   (g) obtaining hematocrit of said blood sample by multiplying said red blood cell concentration obtained in step (f) by said mean cell volume obtained in step (e); and
   (h) reporting said hematocrit of said blood sample.

20. The method of claim 19 wherein said predetermined limit is a channel from or above said red blood cell distribution mode and to below said valley.

21. The method of claim 20 wherein said predetermined limit is about 160 fl.

* * * * *